United States Patent
Zilch et al.

(10) Patent No.: US 6,177,469 B1
(45) Date of Patent: *Jan. 23, 2001

(54) LIPID ALCOHOLS AS NEW IMMUNOSUPPRESSIVE AND ANTIVIRAL DRUGS

(76) Inventors: Harald Zilch, Alsenweg 24, D-68305 Mannheim; Dieter Herrmann, Bothestrasse 54/1, D-69126 Heidelberg; Hans-Georg Opitz, Im Netztal 46, D-69469 Weinheim, all of (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/051,088

(22) PCT Filed: Oct. 11, 1996

(86) PCT No.: PCT/EP96/04438

§ 371 Date: Jun. 22, 1998

§ 102(e) Date: Jun. 22, 1998

(87) PCT Pub. No.: WO97/14410

PCT Pub. Date: Apr. 24, 1997

(30) Foreign Application Priority Data

Oct. 14, 1995 (DE) ............................. 195 38 402

(51) Int. Cl.$^7$ ........................ A61K 37/00; A61K 31/00; A61K 31/14; A61K 31/08
(52) U.S. Cl. ........................ 514/558; 514/506; 514/712; 514/715; 514/722; 514/723
(58) Field of Search .................... 514/558, 506, 514/712, 715, 722, 723

(56) References Cited

U.S. PATENT DOCUMENTS

| | | | |
|---|---|---|---|
| 4,857,511 | * | 8/1989 | Rideout et al. ............... 514/50 |
| 4,997,851 | * | 3/1991 | Isaacs et al. ............... 514/558 |

OTHER PUBLICATIONS

Kemertelidze et al, 113CA:217931, 1990.*
Jia et al, 120CA:245632, 1993.*
Myher et al, 113:CA94136, 1989.*
Itabashi et al, 115:45355, 1990.*
Isaacs et al 112 CA:112053g, 1990.*

* cited by examiner

Primary Examiner—Russell Travers
(74) Attorney, Agent, or Firm—Arent Fox Kintner Plotkin Kahn

(57) ABSTRACT

The present invention concerns new immunosuppressive and antiviral pharmaceutical agents using lipid alcohols of the general formulae I and II

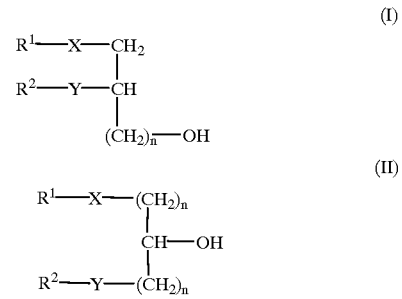

in which
  $R^1$ represents a straight-chained or branched, saturated or unsaturated alkyl chain with 1–30 carbon atoms which can optionally be substituted once or several times by halogen, $C_1$–$C_6$ alkoxy, $C_1$–$C_6$ alkylmercapto, $C_1$–$C_6$ alkoxycarbonyl, carboxy, $C_1$–$C_6$ alkylsulfinyl or $C_1$–$C_6$ alkylsulfonyl groups,
  $R^2$ represents hydrogen, a straight-chained or branched, saturated or unsaturated alkyl chain with 1–20 carbon atoms which can optionally be substituted once or several times by halogen, $C_1$–$C_6$ alkoxy, $C_1$–$C_6$ alkylmercapto, $C_1$–$C_6$ alkoxycarbonyl or $C_1$–$C_6$ alkylsulfonyl groups,
  X represents a valency dash, oxicarbonyl, carbonyloxy, amidocarbonyl, carbonylamido, oxygen, sulphur, a sulfinyl or sulfonyl group
  Y represents a valency dash, oxicarbonyl, carbonyloxy, amidocarbonyl, carbonylamido, oxygen, sulphur, a sulfinyl or sulfonyl group
  n represents an integer value from 1 to 5 inclusive as well as tautomers thereof and combinations containing these compounds with other active substances.

19 Claims, No Drawings

LIPID ALCOHOLS AS NEW IMMUNOSUPPRESSIVE AND ANTIVIRAL DRUGS

This Application is a 371 of PCT/EP96/04438 filed Nov. 15, 1996 which claims Priority From German Patent Applicant 195 38 402,4 filed Oct. 14, 1995

The present invention concerns lipid alcohols as new immunosuppressive and antiviral pharmaceutical agents. Lipid alcohols are known as intermediate products for the production of e.g. phosphocholines or liponucleotides. Such intermediate products are described for example in the following patent applications and literature references: [J. Med. Chem. 34, 1377 (1991), Tetrahedron Lett. 26, 1167 (1985), Gazz. Chim. Ital. 116, 25 (1986), Lipids 22, 947 (1987), EP 90 11 6298, DE 36 38 126, EP 0 050 327]. Lipids with chains interrupted by heteroatoms in phosphocholines are described in DE 39 29 217.7 and WO 91/05558 and the documents EP 0 350 287, WO 90/00555, PCT/EP 93/00294, PCT/EP 93/00295, EP 0545966 and PCT/EP 93/02101 show the use of corresponding lipid moieties as specific carriers in covalent conjugates with nucleoside monophosphates.

In none of the cases is a pharmacological effect of the lipid alcohols used as an intermediate product in the production described.

Even in a routine examination of these compounds for an antiviral action in the known test systems for HIV (e.g. MT2/MTT test or corresponding tests with M/M etc.) no direct antiretroviral effect could be found (up to 100 μg/ml).

The present invention concerns new immunosuppressive and antiviral pharmaceutical agents using lipid alcohols of the general formulae I and II

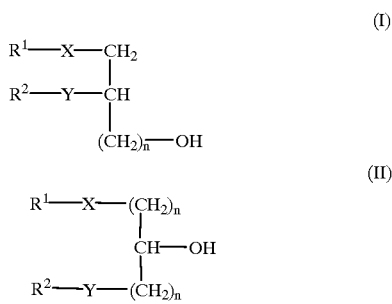

in which
R$^1$ represents a straight-chained or branched, saturated or unsaturated alkyl chain with 1–30 carbon atoms which can optionally be substituted once or several times by halogen, C$_1$–C$_6$ alkoxy, C$_1$–C$_6$ alkylmercapto, C$_1$–C$_6$ alkoxycarbonyl, carboxy, C$_1$–C$_6$ alkylsulfinyl or C$_1$–C$_6$ alkylsulfonyl groups,
R$^2$ represents hydrogen, a straight-chained or branched, saturated or unsaturated alkyl chain with 1–20 carbon atoms which can optionally be substituted once or several times by halogen, C$_1$–C$_6$ alkoxy, C$_1$–C$_6$ alkylmercapto, C$_1$–C$_6$ alkoxycarbonyl or C$_1$–C$_6$ alkylsulfonyl groups,
X represents a valency dash, oxicarbonyls carbonyloxy, amidocarbonyl, carbonylamido, oxygen, sulphur, a sulfinyl or sulfonyl group
Y represents a valency dash, oxicarbonyl, carbonyloxy, amidocarbonyl, carbonylamido, oxygen, sulphur, a sulfinyl or sulfonyl group
n represents an integer from 1 to 5 inclusive, as well as tautomers thereof and combinations containing these compounds with other active substances.

Since the compounds of the general formulae I and II contain asymmetric carbon atoms, all optically active forms and racemic mixtures of these compounds are also a subject matter of the present invention. As far as possible the invention also includes pharmacologically acceptable (acid addition) salts.

R$^1$ in the general formulae I and II is preferably a straight-chained or branched, saturated alkyl chain with 7–18 carbon atoms which can optionally be substituted once or several times by halogen, C$_1$–C$_6$ alkoxy, C$_1$–C$_6$ alkylmercapto or C$_1$–C$_6$ alkylsulfonyl groups. Unbranched saturated alkyl residues with 8–15 carbon atoms are particularly preferred for R$^1$. R$^1$ in particular represents a nonyl, decyl, undecyl, dodecyl, tridecyl or tetradecyl residue.

Methoxy, ethoxy, butoxy and hexyloxy groups come preferably into consideration as C$_1$–C$_6$ alkoxy substituents of R$^1$. If R$^1$ is substituted by a C$_1$–C$_6$ alkylmercapto residue this is in particular understood as a methylmercapto, ethylmercapto, propylmercapto, butylmercapto and hexylmercapto residue.

R$^2$ preferably denotes a straight-chained or branched, saturated alkyl chain with 6–16 carbon atoms which in addition can be substituted by a C$_1$–C$_6$ alkoxy or C$_1$–C$_6$ alkylmercapto group or halogen.

R$^2$ is preferably a straight-chained C$_8$–C$_{15}$ alkyl group which can in addition be substituted by a C$_1$–C$_6$ alkoxy group or a C$_1$–C$_6$ alkylmercapto group. R$^2$ in particular represents an octyl, nonyl, decyl, undecyl, dodecyl, tridecyl or tetradecyl group. A methoxy, ethoxy, propoxy, butoxy and hexyloxy group preferably come into consideration as C$_1$–C$_6$ alkoxy substituents of R$^2$. If R$^2$ is substituted by a C$_1$–C$_6$ alkylmercapto residue this is especially understood as a methylmercapto, ethylmercapto, butylmercapto and hexylmercapto residue.

Compounds of the general formula I are also preferred in which R$^2$ represents a hydrogen atom and Y equals oxygen or a valency dash.

In this case compounds are particularly preferred in which Y is a valency dash, R$^2$ represents hydrogen, X has the meaning stated above and R$^1$ represents an alkyl residue with 12–25 carbon atoms.

An unbranched, saturated C$_{12}$–C$_{25}$ alkyl residue which is bound to the parent substance via X equals sulphur is especially preferred for R$^1$ in these combinations.

X is preferably sulphur, sulfinyl or sulfonyl and Y equals oxygen.

n preferably equals 1 to 3, it, however, particularly preferably equals 1.

The heteroatoms X and Y in the lipid part can only be replaced in special cases by the carboxylic acid esters known from lecithin since otherwise a hydrolytic cleavage to form the corresponding lysolecithin derivatives or glycerol esters would already occur in the serum or in the liver (first pass effect) with a corresponding more rapid elimination of the pharmacologically active substance. The thioether and ether lipids (X, Y=O,S) of this application do not exhibit this cleavage in the serum of various species including humans.

The therapy of malignomas and malignant neoplasias (carcinomas, sarcomas, haematological neoplasias), of inflammatory diseases or organ-specific and generalized autoimmune diseases as well as of diseases caused by (retro)viruses such as AIDS, ARC (AIDS related complex), cytomegaly, herpes or hepatitis is often associated with extreme side-effects in addition to the inadequate efficacy of the therapeutically active substances used. This effect is due to the low in vivo selectivity and the limited therapeutic range of the pharmacologically active substances that are used. The favourable pharmacological in vitro properties of the respective compounds are often not transferable to the in vivo conditions. Therefore for years attempts have been made to provide new substances by modifying the chemical structure of pharmacologically active substances which have improved properties with regard to the therapeutic range. In addition new pharmaceutical forms of administration are often developed with this goal. In this process the intention is in particular to avoid an undesired interaction with healthy cells/tissues.

The compounds according to the invention have shown no toxic effects whatsoever in vitro and in vivo up to the highest concentration and dose tested of 100 $\mu$g/ml and 100 mg/kg.

The compounds of formulae I and II are suitable for the treatment of (retro)viral infections in humans such as persistent generalized lymphoadenopathy (PGL), the advanced stage of the AIDS-related complex (ARC) and the full clinical picture of AIDS.

The inhibitory action on HI viruses (HIV 1 and HIV 1) which are responsible for the immune deficiency disease AIDS is of therapeutic interest. 3'-Azido-3'-deoxythymidine (DE-A-3608606) is today approved for the treatment of AIDS. However, toxic side-effects of 3'-azido-3'-deoxythymidine e.g. on bone marrow limit the use of this medicament. The compounds of the general formulae I and II do not have these disadvantages. They have an antiviral/antiretroviral action without being (cyto)toxic in pharmacologically relevant doses.

The compounds of the present invention and their pharmacological preparations can be used in combination with other pharmaceutical agents for the treatment and prophylaxis of the aforementioned infections. Examples of agents containing further pharmaceutical agents which can be used for the treatment and prophylaxis of HIV infections or diseases accompanying this illness are 3'-azido-3'-deoxythymidine, 2',3'-dideoxynucleosides such as 2',3'-dideoxyinosine, acyclic nucleosides (e.g. Acyclovir) or non-nucleosidic RT inhibitors such as e.g. HEPT, Nevirapin or L-697,661 (MSD) and corresponding derivatives. The compounds of the present invention and the other pharmaceutical agents can be respectively administered individually, simultaneously and optionally in a single or two separate formulations or at different times.

In addition it was also surprisingly found that lipid alcohols of the general formulae I and II also exhibit an immunosuppressive or anti-(retro)viral action. In particular they are suitable for the therapy and prophylaxis of infections which are caused by DNA viruses such as HSV-1, HSV-2, CMV, VZV, EBV, HVB etc. or RNA viruses such as HTLV-I and HTLV-II, HIV-1 and HIV-2, visna, other onco viruses etc.

The compounds of the general formulae I and II have surprisingly shown an antiviral/antiretroviral in vitro activity which, although not directly inhibiting the replication of DNA and RNA viruses, influences the infectiousness of the virus particles that are formed. The replication is influenced by the claimed compounds by inhibition of the virus assembly in such a way that almost only non-infectious virus particles are released.

This effect could for example also be demonstrated in vivo in the Friend virus leukemia (FVL) model in the mouse e.g. for retroviruses.

In addition a synergistic effect with AZT among others reverse transcriptase (RT) and non-RT inhibitors could be shown in the FVL model. Simultaneous treatment with non-active individual doses of the lipid alcohol and the nucleoside or RT inhibitors, non-RT inhibitors etc. showed clear synergistic effects on the survival time of FVL-infected mice.

The lipid alcohols of the general formulae I and II all have a large therapeutic range, they have a very long retention time in the body, the bioavailability is very good and the membrane permeability (e.g. cell membrane, blood-brain barrier etc.) which is known to be often a critical factor is also well above average. The compounds only have a slow elimination and do not have any bone marrow or other limiting organ toxicities in pharmacologically/therapeutically relevant dose ranges.

In particular the claimed compounds are suitable for the therapy of the stated diseases in combination with other pharmaceutical agents/active substances.

The pharmacologically active substance used for the combination can for example have a cytostatic, cytotoxic, antitumoural, antiviral, antiretroviral, immunosuppressive or immunostimulating action.

A suitable pharmacologically active substance is a compound which for example slows tumour growth, a substance which intercalates in DNA and/or RNA, inhibits topoisomerase I and II, is a tubulin inhibitor, is an alkylating agent, is a ribosome inactivating compound, is a tyrosine phosphokinase inhibitor, is a differentiation inducer, a hormone, hormone agonist or hormone antagonist, is a substance which changes the pleiotropic resistance to cytostatic agents, is a calmodulin inhibitor, is a protein kinase C inhibitor, is a P-glucoprotein inhibitor, is a modulator of the mitochondrially bound hexokinase, is an inhibitor of $\gamma$-glutamylcysteine synthetase or glutathione S-transferase, is an inhibitor of superoxide dismutase, is an inhibitor of the reverse transcriptase of HIV-1 and HIV-2.

In addition to the pharmacologically active substance can also have an anti-inflammatory, antirheumatic, antiphlogistic, analgetic or antipyretic action. In addition it can be an anti-arrhythmic drug, calcium antagonist, antihistamic agent, an inhibitor of phosphodiesterase or a sympathomimetic/sympatholytic agent or parasympathomimetic/parasympatholytic agent. In addition those substances are suitable which specifically interact with the cell nucleus of the target cells and interfere with the molecular processes at the DNA or RNA level such as e.g. (anti)sense oligonucleotides, DNA fragments and those which can be used for gene therapy.

Pharmacologically active substances for the combination are for example:

AZT (azidothymidine), FLT (fluorothymidine), 5-FU (5-fluorouridine), 6-MPR, Fludarabin, Cladribin, Pentostatin, ara-C, ara-A, ara-G, ara-H, Acylclovir, Ganciclovir, Doxorubicin, 4'-epi-Doxorubicin, 4'-deoxy-Doxorubicin, Etoposide, Daunomycin, Idarubicin, Epirubicin, Mitoxantron, Vincristin, Vinblastin, Taxol, Colchicin, Melphalan, 3'-deoxy-2-fluoradenosine, FdA, 5ethinyluracil-9-$\beta$-D-arabinofuranoside, 5-propinyluracil-9-$\beta$-D-arabinofuranoside, d4T, ddU, ddI, ddA, d2T, 2'-deoxy-2',2'-difluorocytidine, 5-trifluoromethyl-2'deoxyuridine, 5-chloro-2',3'-dideoxy-3'-fluorouridine, 3'-deoxy-3'-fluoro-myoinositol, Neplanocin A, Ribavirin, myoinositol, fialuridine, 3TC, Lamivudin, Doxifluridin, Tegafur, Hypericin, pseudohypericin, Usevir, Famciclovir, Penciclovir, Carvedilol, Actinomycin A, Bleomycin, Daunorubicin, floxuridine, Mithramycin, Mitomycin C, Mitoxanthron, Streptozotocin, Vindesin, Netilmycin, Amikacin, gentamycin, streptomycin, kanamycin A, tobramycin, neomycin B, plicamycin, amphotericin B, vancomycin, Foscarnet, idoxuridine, trifluridin, Vidarabin as well as morphines, prostaglandins, leukotrienes or cyclosporines. In addition the following come into consideration: Terfenadin, dexamethasone; terbutalin; prednisolone; fenoterol; orciprenaline; salbutamol; isoprenaline; muscarin; bupranolol; oxyphenbutazone; oestrogen; salicylic acid; propanolol; ascorbic acid: spongiadiol; Diclofenac, isospongiadiol; flufenaminic acid; digoxin; 4-methylaminophenazone; allopurinol; theophyllin; epoprostenol; nifedipin; quinine; reserpine; methotrexate; chlorambucil; spergualin; ibuprofen; indomethacin; sulfasalazine; penicillanamin; chloroquin; thalidomide.

Preferred pharmacologically active substances are also for example peptides, proteins and oligonucleotides such as e.g. corticotropin, calcitonin, desmopressin, gonadotropin, goserelin, insulin, Zypressin, beta-melanotropin, alpha-melanotropin, muramyldipeptide, oxytocin, vasopressin, FK-506, cyclosporins, octreotide or enalkirene.

The above-mentioned pharmacologically active substances and the combinations which can be prepared therefrom represent new examples and do not limit the inventive idea.

The compounds of the present invention are also suitable for the treatment and prophylaxis of malignomas, neoplasms, carcinomas, sarcomas or leukaemias.

The compounds also have an immunosuppressive action and can therefore be used for the treatment of organ-specific or generalized autoimmune diseases such as rheumatoid arthritis, system ic lupus erythematosus, chronic graft versus host disease, multiple sclerosis etc. or to prevent allogenic or semiallogenic transplant rejections such as of the kidney, liver, lung, heart etc.

Compared to the compounds that have previously been used to treat malignant tumours, the compounds according to the invention have a significantly lower toxicity and thus a larger therapeutic range in addition to a good efficacy. They therefore have the advantage that these compounds can be administered continuously over a long period in the form of their pharmaceutical formulations and thus avoid discontinuation of the preparation or an intermittent administration which is common for the cytostatic agents that are used nowadays in tumour therapy or which is unavoidable due to their undesired side-effects.

The compounds accord ing to the invention have an immunosuppressive or antitumoral action without being unspecifically (cyto)toxic in pharmacologically relevant doses.

The advan tages of the compounds acc ording to the invention are also seen in combination with other antiviral/antiretroviral, immunosuppressive or antitumoral pharmaceutical agents/active substances.

Due to a synergistic effect of the lipid alcohols of formulae I or II with e.g. nucleosides, the proportionate dose of these compounds that are usually toxic in higher doses can be lowered and thus undesired side-effects can be alleviated or in some cases completely eliminated.

The combination can fundamentally be an alternating or a simultaneous dose of lipid alcohol and the active substance which is to be combined with it. The lipid alcohol can also be present in the form of a prodrug i.e. it is firstly converted metabolically in vivo in combinations of formulae I and II. Such prodrugs of formula I are preferred in which the hydroxy group of the glycerol forms a phosphate ester or pyrophosphate ester. The phosphate group or pyrophosphate group can also be esterifdied again.

In many diseases such as e.g. AIDS, tumour diseases etc. the combination of a lipid alcohol of formulae I and II with more than one additional pharmaceutical agent/active substance can be of additional advantage when for example resistance develops.

A combination of a) lipid alcohol of formulae I or II b) nucleoside and c) non-nucl eosidic RT inhibit or, protease inhibitor or tat inhibitor has for example a therapeutic advantage over the respective monotherapy for the treatment of AIDS patients.

Appropriate comparative experiments have been able to show that the therapeutic effects of the known diacylglycerols are inferior in vivo to the thioether or ether lipid alcohols of this application. This is due to an unspecific hydrolysis of the fatty acid esters. In contrast the non-hydrolyzable thioether and ether residues are metabolically stable.

The lipid alcohol with its lecithin-like structure which is essential for the claimed effect shows a good membrane permeability (readily surmounting the resorption barriers) and a depot effect when the chain length is optimal.

In addition the distribution in vivo is improved by the high binding of the compounds according to formulae I and II to plasma and tissue proteins. Due to normal biotransformation the lipid alcohol is primarily oxidized from the thioester (X=S) to the sulfoxide (X=SO) which, however, due to the equipotent action of the sulfoxide compared to the thioester, is not a therapeutic disadvantage. A slow release from intracellular or membrane compartments ensures a slow but constant level of substance over a long time period thus improving the action or avoiding toxic sideeffects.

The compounds of formulae I and II can be used as active substances to produce pharmaceutical agents or the intrinsic action of one of the compounds according to the invention is increased further by combination with other pharmaceutical agents for the treatment and prophylaxis of various diseases.

Compounds of formulae I and II and their use as intermediate products are described in the applications WO 92/03462, WO 93/16092, WO 93/16091, WO 94/03465, PCT/EP 94/02123, DE 4402492, DE 4418690 as well as for example in WO 91/19726; EP 0 350 287; U.S. Pat. No. 5,223,263; U.S. Pat. No. 5,194,654; U.S. Pat. No. 4,921,951; U.S. Pat. No. 4,622,392; U.S. Pat. No. 4,291,024; U.S. Pat. No. 4,283,394.

The compounds of the general formulae I and II are also produced analogously to Lipids 22, 947 (1987), and J. Med. Chem. 34, 1377 (1991) as well the literature cited in the state of the art.

In addition the following synthesis starting with glycerol which is shown for a special example has proven to be successful:

glycerol + benzaldehyde

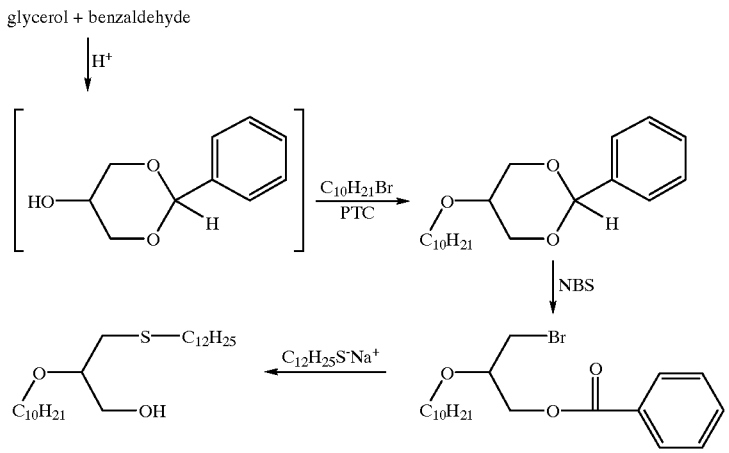

The thioether obtained in this way (or a derivative prepared in an analogous manner with a modified chain length) can subsequently be oxidized to the corresponding sulfoxide or sulfone by a method known to a person skilled in the art.

The pharmaceutical agents containing compounds of formulae I and II for the treatment of viral infections can be administered enterally or parenterally in a liquid or solid form. In this connection all the usual forms of administration come into consideration such as for example tablets, capsules, coated tablets, syrups, solutions or suspensions. Water which contains additives such as stabilizers, solubilizers and buffers that are usual in injection solutions is preferably used as the injection medium. Such additives are e.g. tartrate and citrate buffer, ethanol, complexing agents such as ethylenediaminetetraacetic acid and non-toxic salts thereof, high-molecular polymers such as liquid polyethylene oxide to regulate viscosity.

Liquid carrier substances for injection solutions have to be sterile and are preferably filled into ampoules. Solid carrier substances are for example starch, lactose, mannitol, methylcellulose, talcum, highly dispersed silicic acids, higher molecular fatty acids such as stearic acid, gelatins, agar-agar, calcium phosphate, magnesium stearate, animal and vegetable fats, solid high-molecular polymers such as polyethylene glycols etc. Suitable preparations for oral applications can optionally also contain flavourings and sweeteners.

The dosage can depend on various factors such as manner of administration, species, age and individual state. The compounds according to the invention are usually administered in amounts of 1–100 mg preferably 2–80 mg per day and per kg body weight. It is preferable to distribute the daily dose over 1–3 administrations in which case 1–2 tablets are administered for each application with an active substance content of 5–500 mg. The tablets can also be retarded by which means the number of administrations is reduced to 1–2 per day. The active substance content of the retarded tablets can be 2–2000 mg. The active substance can also be administered by means of a continuous infusion in which amounts of 5–3000 mg per day are usually adequate.

Within the sense of the present invention the following compounds of formula I come into consideration in addition to the compounds mentioned in the examples and compounds which can be derived by combining all meanings of substituents mentioned in the claims:

2-butylmercaptomethyl-1-octadecanol
2-decyloxy-1-tetradecanol
2-dodecyloxy-1-tetradecanol
2-dodecylmercapto-1-tetradecanol
2-dodecylmercaptomethyl-1-tridecanol
3-dodecylmercapto-2-decanoyloxy-1-propanol
2,3-bis-(octadecanoyl)-1-propanol
4-dodecylmercapto-3-decyloxy-1-butanol
4-undecylmercaptor-3-undecyloxy-1-butanol
5-dodecylmercapto-4-decyloxy-1-pentanol
1,3-bis-(dodecylmercapto)-2-propanol
3-dodecanoylamino-2-undecyloxy-1-propanol
1-dodecylmercapto-3-decyloxy-2-propanol
3-dodecanoylamino-2-decyloxy-1-propanol
(R)-3-dodecylmercapto-2-decyloxy-1-propanol
(S)-3-dodecylmercapto-2-decyloxy-1-propanol

EXAMPLE 1

5-Decyloxy-2-phenyl-1,3-dioxane 92 g Glycerol was heated for 2.5 hours with 106 g (101 ml) benzaldehyde with catalysis of 1 ml methanesulfonic acid in 330 ml toluene on a water separator under reflux (18 ml water separated).

The clear solution was cooled to room temperature, admixed with 500 ml isohexane and stirred for 2–3 hours in an ice-bath (thick, white precipitate, eventually more isohexane necessary).

After addition of 1 l concentrated NaOH and 670 ml toluene the isohexane was distilled to a transition temperature of 90° C. (ca. 700 ml distillate). The twophase solution was then admixed with 332 ml bromodecane and 11.8 g Aliquat and stirred for a further two hours at 85–90° C. internal temperature.

After cooling the aqueous phase was separated, the organic phase was extracted four times with 1 l water each time and the toluene was removed by distilling up to 150° C. outside temperature and 1 mbar.

The residue was dissolved in 2 l isohexane, carbonized with 10 g Brilonit, aspirated and crystallized at −20° C. overnight. The precipitate was suction filtered at a low temperature, washed with 100 ml cold isohexane and dried in a vacuum at room temperature.

Yield: 261 g/81% of theory. GC: 95.21 area %

Benzoic acid-(3-bromo-2-decyloxy-propyl)ester 72.6 g 5-Decyloxy-2-phenyl-1,3-dioxane was dissolved in 480 ml isohexane, admixed with 1.36 g calcium oxide as well as with 39 g N-bromosuccinimide and stirred for 4 hours at 40° C.

It was then cooled to 20° C., admixed with 10 g active charcoal and the charcoal is removed by filtration after stirring for 10 minutes.

The filtrate was evaporated in a vacuum at <30° C. and the residue was used directly in the next reaction without further purification.

Crude yield: 89 g, GC: 92.6%, step I: 0.87%
3-Dodecylmercapto-2-decyloxy-1-propanol 55 ml 1-Dodecylmercaptane in 64 ml methanol was admixed within 5 minutes with a solution of 43 ml 30% sodium methylate solution in 325 ml methanol and stirred for 30 minutes at ca. 25° C. 89 g of the crude product was then added to the last reaction in 140 ml methanol and the solution was stirred for a further 15 hours at 20–25° C.

Subsequently 52 ml 2 N hydrochloric acid was added, stirred for a further hour at 35–40° C. and the solution was cooled to 20° C. It was stirred for 2 hours at 40–45° C. after addition of 28 ml 50% sodium hydroxide solution, the methanol was removed in a vacuum at 100 mbar at a maximum of 55° C. and extracted with 480 ml MTB after diluting with 480 ml water. The organic phase was separated, washed with saturated sodium chloride solution and water and the solvent was removed in a vacuum. The residue (90 g crude) was purified chromatographically on silica gel 60 using toluene/MTB 20/1 as the eluent. 78.8 g oil was isolated from the fractions containing product after removing the solvent in a rotary evaporator. GC: 96%.

EXAMPLE 2

Efficacy and Balance in the Friend-virus-leukemia Model

Female Balb/c mice, 6–8 weeks old (Iffa Credo) were inoculated intraperitoneally on day 0 with 0.2 ml per animal of a spleen supernatant containing viruses. The animals were treated intraperitoneally with the substance to be examined in doses of 6.25 mg, 12.5 mg, 25 mg and 50 mg per kg beginning at day 0 (start: 1 hour after virus inoculation) up to day 13.

Before the start of the treatment as well as on day 13 the parameters body weight and small blood count (WBC, RBC, Hb, Hct, Plt) and on day 14 after sacrificing the animals the individual weights of the spleens were determined as a parameter for viraemia.

EXAMPLE 3

Efficacy in an HIV-infected Cell Culture

As a routine triple determinations were carried out nearly automatically (Biomek from Beckmann) in microtitre plates in an MT2-system using at least 4 concentrations (standard deviation <5%). The toxicity (cells+substance) and the antiviral efficacy (cells+substance+virus) were determined in parallel preparations.

MT2 cells were pre-incubated with the substance to be examined and infected with HIV-1 (HTLV-III-B, MOI 0.03). The supernatant was removed, replaced by medium (including substance) and incubated for 7 days.

Afterwards it was evaluated according to cytopathic effect (syncytia), MTT test (vitality of the cells) and the supernatant was transferred for a renewed infection.

EXAMPLE 4

The following compounds were prepared analogously to example 1:
1. 3-undecylmercapto-2-decyloxy-1-propanol
2. 3-tridecylmercapto-2-decyloxy-1-propanol
3. 3-undecylmercapto-2-undecyloxy-1-propanol
4. 3-decylmercapto-2-dodecyloxy-1-propanol
5. 3-undecylmercapto-2-dodecyloxy-1-propanol
6. 3-dodecylmercapto-2-dodecyloxy-1-propanol
7. 3-dodecylmercapto-2-undecyloxy-1-propanol
8. 3-dodecylmercapto-2-decylmercapto-1-propanol
9. 2,3-bis-(undecylmercapto)-1-propanol
10. 2,3-bis-(undecyloxy)-1-propanol
11. 3-dodecyloxy-2-decyloxy-1-propanol
12. 3-tridecyloxy-2-decyloxy-1-propanol
13. 3-decyloxy-2-dodecyloxy-1-propanol
14. 3-pentadecylmercapto-2-decyloxy-1-propanol
15. 3-octylmercapto-2-decyloxy-1-propanol
16. 3-decylmercapto-2-octyloxy-1-propanol
17. 3-decylmercapto-2-dodecylmercapto-1-propanol
18. 3-dodecyloxy-2-decylmercapto-1-propanol
19. 3-decyloxy-2-dodecylmercapto-1-propanol
20. 3-dodecylmercapto-2-octyloxy-1-propanol
21. 3-decylmercapto-2-decyloxy-1-propanol
22. 3-tetradecylmercapto-2-decyloxy-1-propanol
23. 2,3-Bis-(octylmercapto)-1-propanol
24. 3-hexadecylmercapto-2-decyloxy-1-propanol
25. 3-decylmercapto-2-hexadecyloxy-1-propanol
26. 3-hexadecylmercapto-2-hexadecyloxy-1-propanol
27. 2,3-Bis-(decyloxy)-1-propanol
28. 3-hexadecylmercapto-2-cyclohexyloxy-1-propanol
29. 3-(9-phenyl-nonylmercapto)-2-decyloxy-1-propanol
30. 3-dodecylmercapto-2-(9-phenyl-nonyloxy)-1-propanol
31. 3-(1-methyl-undecyl)mercapto-2-decyloxy-1-propanol
32. 3-(1-butyl-octyl)mercapto-2-decyloxy-1-propanol

EXAMPLE 5

3-Dodecysulfinyl-2-decyloxy-1-propanol 10 g 3-Dodecylmercapto-2-decyloxy-1-propanol was dissolved in 100 ml glacial acetic acid and stirred for 4 hours at room temperature after addition of 10 ml 30% hydrogen peroxide. The solvent was then removed on a rotary evaporator and the residue was purified chromatographically on silica gel 60 using ether/isohexane 1:2 as the eluent. The fractions containing product were evaporated and yielded 7.4 g of the desired sulfoxide as an oil.

EXAMPLE 6

The following comnpounds were prepared analogously to example 5
1. 3-undecylsulfinyl-2-decyloxy-1-propanol
2. 3-tridecylsulfinyl-2-decyloxy-1-propanol
3. 3-undecylsulfinyl-2-undecyloxy-1-propanol
4. 3-decylsulfinyl-2-dodecyloxy-1-propanol
5. 3-undecylsulfinyl-2-dodecyloxy-1-propanol
6. 3-dodecylsulfinyl-2-dodecyloxy-1-propanol
7. 3-dodecylsulfinyl-2-undecyloxy-1-propanol

EXAMPLE 7

3-Dodecylsulfonyl-2-decyloxy-1-propanol 10 g 3-Dodecylmercapto-2-decyloxy-1-propanol was dissolved in 100 ml glacial acetic acid and stirred for 6 hours at 50° C. after addition of 25 ml 30% hydrogen peroxide. Subsequently a further 13 ml hydrogen peroxide was added and it was stirred for a further 7 hours. The solvent was then removed on a rotary evaporator and the residue was purified chromatographically on silica gel 60 using ether/isohexane 1:1.5 as the eluent. The fractions containing product were evaporated and yielded 8 g of the desired sulfone as an oil.

EXAMPLE 8

The following compounds were prepared analogously to example 7:
1. 3-undecylsulfonyl-2-decyloxy-1-propanol
2. 3-tridecylsulfonyl-2-decyloxy-1-propanol
3. 3-undecylsulfonyl-2-undecyloxy-1-propanol
4. 3-decylsulfonyl-2-dodecyloxy-1-propanol
5. 3-undecylsulfonyl-2-dodecyloxy-1-propanol
6. 3-dodecylsulfonyl-2-dodecyloxy-1-propanol
7. 3-dodecylsulfonyl-2-undecyloxy-1-propanol

EXAMPLE 9
1,3-Bis-(dodecylmercapto)-2-propanol 26.6 ml Dodecanethiol was added to an ethylate solution of 2.6 g sodium in 100 ml ethanol and the solution was stirred for 1 hour at room temperature. Then 8.5 ml epibromohydrin was added dropwise within 30 min and stirred overnight. The residue was taken up in ether after removing the solvent, washed twice with water and dried. The desired compound crystallized on evaporation of the solution. Yield 28.5 g (62%).

EXAMPLE 10
1-Dodecylmercapto-3-decyloxy-2-propanol

A mixture of 9.52 ml 1-decanol, 4.23 ml epibromohydrin and 3.4 g tetrabutylammonium hydrogen sulfate in 150 ml dichloromethane and 150 ml 50% sodium hydroxide solution was stirred for 3 hours at room temperature. The organic phase was then separated, washed twice with water and evaporated. The residue was purified chromatographically on silica gel 60 with ether/isohexane 1:15 as the eluant. Yield 5.4 g oil.

After dissolving in 30 ml ethanol this oil was admixed with a mercaptide solution which had previously been prepared by reacting 1.94 ml 1-dodecylmercaptan in 20 ml ethanol with sodium methylate. After stirring overnight at room temperature, the solvent was removed by distillation, the residue was taken up in dichloromethane, washed twice with water and the organic phase was evaporated. The residue was purified by chromatography on silica gel 60 using ether/isohexane 1:5 as the eluant. Yield 3.9 g.

EXAMPLE 11
2-Decyloxy-1-tetradecanol

A suspension of 1.2 g sodium hydride 90% in 21 ml DMF was admixed within 15 min with 8.5 ml 1-decanol in 30 ml DMF and stirred for a further hour. Then 15 g 2-bromotetradecanoic acid methyl ester was added dropwise in 48 ml toluene and the solution was stirred for 24 hours at room temperature. After removing the solvent by evaporation the residue was taken up in ether, washed with water and the organic phase was evaporated. Residue 18.9 g.

The oil was dissolved in 200 ml ether, admixed with 1.3 g lithium aluminium hydride and heated for 1 hour under reflux. It was then hydrolyzed and the ether phase was evaporated. The residue (17.4 g) was purified by column chromatography on silica gel 60 using ether/isohexane 1:4 as the eluant. Yield 4.26 g.

EXAMPLE 12

2-Dodecyloxy-1-tetradecanol was obtained by reaction with dodecanol analogously to example 11.

EXAMPLE 13

The cell cytotoxicity and the anti-HIV-1-activity in CEM-SS cells of selected lipid alcohols are stated in table 1.

| Compound | IC$_{50}$ ($\mu$M) cytotoxicity | anti-HIV-1 | Diff. selectivity |
|---|---|---|---|
| 3-dodecylsulfinyl-2-decyloxy-1-propanol | 36.76 | 0.18 | 204.22 |
| 3-dodecylsulfonyl-2-decyloxy-1-propanol | 32.68 | 0.54 | 60.52 |
| 3-tetradecylmercapto-2-decyloxy-1-propanol | >100 | >20.0 | ND |
| 3-dodecylmercapto-2-dodecyloxy-1-propanol | >100 | >20.0 | ND |
| 3-dodecylmercapto-2-octyloxy-1-propanol | >90.6 | 7.01 | >12.92 |
| 3-(2-methyl-undecyl)mercapto-2-decyloxy-1-propanol | >100 | 51.25 | >1.95 |
| 3-undecylmercapto-2-undecyloxy-1-propanol | >100 | 2.95 | >33.90 |

The cytotoxicity was determined by uptake of TdR-$^3$H into the total DNA at various concentrations of the stated compounds. The anti-HIV 1 activity was determined using a standard plaque assay of a CEM-SS cell monolayer. The differential selectivity results from the quotient of the IC$_{50}$ and anti-HIV 1 activity concentrations. ND means not determined.

What is claimed is:

1. A pharmaceutical composition, comprising a compound of formula I or II

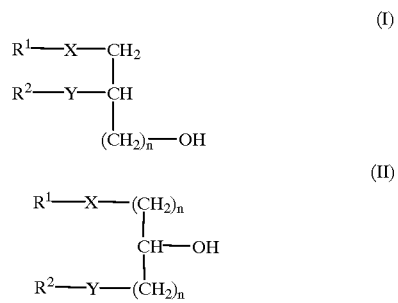

wherein
R$^1$ is a straight-chained or branched, saturated or unsaturated C$_1$–C$_{30}$ alkyl, which is unsubstituted or has at least one substituent each independently selected from the group consisting of halogen, C$_1$–C$_6$ alkoxy, C$_1$–C$_6$ alkylmercapto, C$_1$–C$_6$ alkoxycarbonyl, carboxy, C$_1$–C$_6$ alkylsulfinyl and C$_1$–C$_6$ alkylsulfonyl; and R$^2$ is hydrogen or a straight-chained or branched, saturated or unsaturated C$_1$–C$_{20}$ alkyl, which is unsubstituted or has at least one substituent each independently selected from the group consisting of halogen, C$_1$–C$_6$ alkoxy, C$_1$–C$_6$ alkylmercapto, C$_1$–C$_6$ alkoxycarbonyl and C$_1$–C$_6$ alkylsulfonyl, provided, however, that either R$^1$ is a straight-chained or branched, saturated C$_7$–C$_{18}$ alkyl, which is unsubstituted or has at least one substituent each independently selected from the group consisting of halogen, C$_1$–C$_6$ alkoxy, C$_1$–C$_6$ alkylmercapto and C$_1$–C$_6$ alkylsulfonyl; or R$^2$ is a straight-chained or branched, saturated C$_6$–C$_{16}$ alkyl, which is unsubstituted or has at least one substituent each independently selected from the group consisting of halogen, C$_1$–C$_6$ alkoxy and C$_1$–C$_6$ alkylmercapto;

X is selected from the group consisting of a bond, oxycarbonyl, carbonyloxy, amidocarbonyl, carbonylamido, oxygen, sulfur, sulfinyl and sulfonyl;

Y is selected from the group consisting of a bond, oxycarbonyl, carbonyloxy, amidocarbonyl, carbonylamido, oxygen, sulfur, sulfinyl and sulfonyl; and n is 1–5, or a tautomer or optically active form thereof, in combination with a pharmaceutically acceptable carrier.

2. The pharmaceutical composition of claim 1, wherein $R^1$ is an unbranched saturated $C_8$–$C_{15}$ alkyl.

3. The pharmaceutical composition of claim 1, wherein $R^1$ is an unbranched saturated $C_9$–$C_{14}$ alkyl.

4. The pharmaceutical composition of claim 1, wherein $R^2$ is a straight-chained $C_8$–$C_{15}$ alkyl which is unsubstituted or substituted by $C_1$–$C_6$ alkoxy or $C_1$–$C_6$ alkylmercapto.

5. The pharmaceutical composition of claim 1, wherein $R^2$ is a straight-chained saturated $C_8$–$C_{14}$ alkyl.

6. The pharmaceutical composition of claim 1, wherein $R^2$ is hydrogen and Y is a bond or oxygen.

7. The pharmaceutical composition of claim 1, wherein $R^1$ is a $C_{12}$–$C_{25}$ alkyl, $R^2$ is hydrogen and Y is a bond.

8. The pharmaceutical composition of claim 1, wherein $R^1$ is an unbranched, saturated $C_{12}$–$C_{25}$ alkyl and X is sulfur.

9. The pharmaceutical composition of claim 1, wherein X is selected from the group consisting of sulfur, sulfinyl and sulfonyl.

10. The pharmaceutical composition of claim 1, wherein Y is oxygen.

11. The pharmaceutical composition of claim 1, wherein n is 1–3.

12. The pharmaceutical composition of claim 1, wherein n is 1.

13. The pharmaceutical composition of claim 1, further comprising an additional active substance.

14. The pharmaceutical composition of claim 13, wherein the additional active substance is selected from the group consisting of:

AZT (azidothymidine), FLT (fluorothymidine), 5-FU (5-fluorouridine), 6-MPR, Fludarabin, Cladribin, Pentostatin, ara-C, ara-A, ara-G, ara-H, Acyclovir, Ganciclovir, Doxorubicin, 4'-epi-Doxorubicin, 4'-deoxy-Doxorubicin, Etoposide, Daunomycin, Idarubicin, Epirubicin, Mitoxantron, Vincristin, Vinblastin, Taxol, Colchicin, Melphalan, 3'-deoxy-2-fluoradenosine, FdA, 5-ethinyluracil-9-β-D-arabinofuranoside, 5-propinyluracil-9-β-D-arabinofuranoside, d4T, ddU, ddI, ddA, d2T, 2'-deoxy-2',2'-difluorocytidine, 5-trifluoromethyl-2'-deoxyuridine, 5-chloro-2',3'-dideoxy-3'-fluorouridine, 3'-deoxy-3'-fluoro-myoinositol, Neplanocin A, Ribavirin, myoinositol, fialuridine, 3TC, Lamivudin, Doxifluridin, Tegafur, Hypericin, pseudohypericin, Usevir, Famciclovir, Penciclovir, Carvedilol, Actinomycin A, Bleomycin, Daunorubicin, floxuridine, Mithramycin, Mitomycin C, Mitoxanthron, Streptozotocin, Vindesin, Netilmycin, Amikacin, gentamycin, streptomycin, kanamycin A, tobramycin, neomycin B, plicamycin, amphotericin B, vancomycin, Foscarnet, idoxuridine, trifluridin, Vidarabin, a morphine, a prostaglandin, aleukotriene, a cyclosporine, Terfenadin; dexamethasone; terbutalin; prednisolone; fenoterol; orciprenaline; salbutamol; isoprenaline; muscarin; bupranolol; oxyphenbutazone; oestrogen; salicylic acid; propanolol; ascorbic acid; spongiadiol; Diclofenac, isospongiadiol; flufenaminic acid; digoxin; 4-methylaminophenazone; allopurinol; theophyllin; epoprostenol; nifedipin; quinine; reserpine; methotrexate; chlorambucil; spergualin; ibuprofen; indomethacin; sulfasalazine; penicillanamin; chloroquin; thalidomide;

corticotropin, calcitonin, desmopressin, gonadotropin, goserelin, insulin, Zypressin, beta-melanotropin, alpha-melanotropin, muramyldipeptide, oxytocin, vasopressin, FK-506, octreotide and enalkirene.

15. The pharmaceutical composition of claim 1, wherein the compound is selected from the group consisting of:

2-butylmercaptomethyl-1-octadecanol, 2-decyloxy-1-tetradecanol, 2-dodecyloxy-1-tetradecanol, 2-dodecylmercapto-1-tetradecanol, 2-dodecylmercaptomethyl-1-tridecanol, 3-dodecylmercapto-2-decanoyloxy-1-propanol, 2,3-bis-(octadecanoyl)-1-propanol, 4-dodecylmercapto-3-decyloxy-1-butanol, 4-undecylmercaptor-3-undecyloxy-1-butanol, 5-dodecylmercapto-4-decyloxy-1-pentanol, 1,3-bis-(dodecylmercapto)-2-propanol, 3-dodecanoylamino-2-undecyloxy-1-propanol, 1-dodecylmercapto-3-decyloxy-2-propanol, 3-dodecanoylamino-2-decyloxy-1-propanol, (R)-3-dodecylmercapto-2-decyloxy-1-propanol and (S)-3-dodecylmercapto-2-decyloxy-1-propanol.

16. A method of treating a condition selected from the group consisting of viral or retroviral infection, malignoma, neoplasia, inflammatory disease and autoimmune disease in a patient in need of such treatment, the method comprising administering to the patient a condition-treating effective amount of a pharmaceutical composition as claimed in claim 1.

17. The method of claim 16, wherein the viral or retroviral infection is caused by a virus selected from the group consisting of HSV-1, HSV-2, CMV, VZV, EBV, HVB, HTLV-I, HTLV-II, HIV-1, HIV-II, visna and an oncovirus.

18. A method of treating a condition selected from the group consisting of viral or retroviral infection, malignoma, neoplasia, inflammatory disease and autoimmune disease in a patient in need of such treatment, the method comprising administering to the patient a condition-treating effective amount of a pharmaceutical composition as claimed in claim 13.

19. The method of claim 18, wherein the viral or retroviral infection is caused by a virus selected from the group consisting of HSV-1, HSV-2, CMV, VZV, EBV, HVB, HTLV-I, HTLV-II, HIV-1, HIV-II, visna and an oncovirus.

* * * * *